United States Patent [19]
Kahn et al.

[11] 3,938,198
[45] Feb. 17, 1976

[54] HIP JOINT PROSTHESIS

[75] Inventors: Paul Kahn, San Francisco; James A. Stubstad, Lafayette, both of Calif.

[73] Assignee: Cutter Laboratories, Inc., Berkeley, Calif.

[22] Filed: Sept. 27, 1973

[21] Appl. No.: 401,506

Related U.S. Application Data

[63] Continuation of Ser. No. 162,936, July 15, 1971, abandoned, and a continuation-in-part of Ser. No. 60,804, Aug. 4, 1970, abandoned.

[52] U.S. Cl.................. 3/1.912; 3/1.913; 128/92 C; 128/92 CA
[51] Int. Cl.² .......................................... A61F 1/24
[58] Field of Search .................. 3/1, 1.9–1.913; 128/92 C, 92 CA, 92 R, 92 D, DIG. 21

[56] References Cited
UNITED STATES PATENTS

| | | | |
|---|---|---|---|
| 2,679,245 | 5/1954 | Timmermans.................. | 128/92 CA |
| 3,462,765 | 8/1969 | Swanson ................................. | 3/1.91 |
| 3,593,342 | 7/1971 | Niebauer et al. ...................... | 3/1.91 |
| 3,623,164 | 11/1971 | Bokros..................................... | 3/1.9 |
| 3,623,212 | 11/1971 | Child ........................................ | 3/1.5 |

FOREIGN PATENTS OR APPLICATIONS

| | | | |
|---|---|---|---|
| 1,047,640 | 7/1953 | France ............................... | 128/92 C |
| 939,226 | 2/1956 | Germany........................... | 128/92 C |

OTHER PUBLICATIONS

"Silicone Rubber Implants for Replacement of Arthritic or Destroyed Joints in the Hand" by A. Swanson, Surgical Clinics of North America, Vol. 48, No. 5, Oct. 1968, pp. 1113–1127.

*Primary Examiner*—Ronald L. Frinks
*Attorney, Agent, or Firm*—Owen, Wickersham & Erickson

[57] ABSTRACT

A prosthesis for replacement of a damaged joint or load-bearing structure in an animal or human body comprises a shaped structural member, a relatively thick or cushioning coating of a physiologically inert elastomer over the surfaces of the structural member in load-bearing relationship with the skeletal structure of the body, and an open-pore, tissue-ingrowth-receptive fabric coating the elastomer, all elements being firmly bonded to each other. In many embodiments, a stem of the prosthesis comprising the above elements is adapted to be inserted into a bone cavity, and is eventually affixed firmly thereto by fibrous tissue and bony ingrowth. Stability of the stem portion is enhanced by buttresses integral with the base of the stem.

6 Claims, 9 Drawing Figures

U.S. Patent  Feb 17, 1976  Sheet 1 of 3  3,938,198
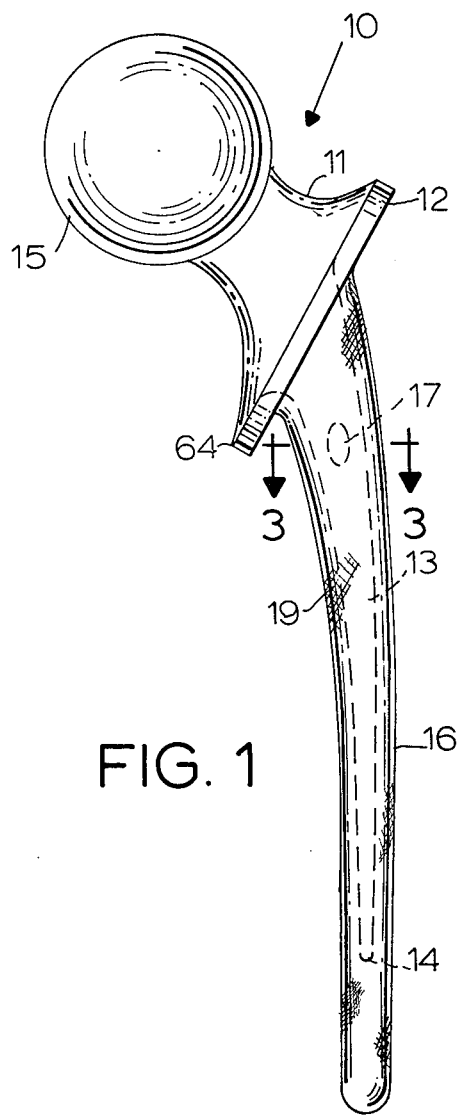
FIG. 1
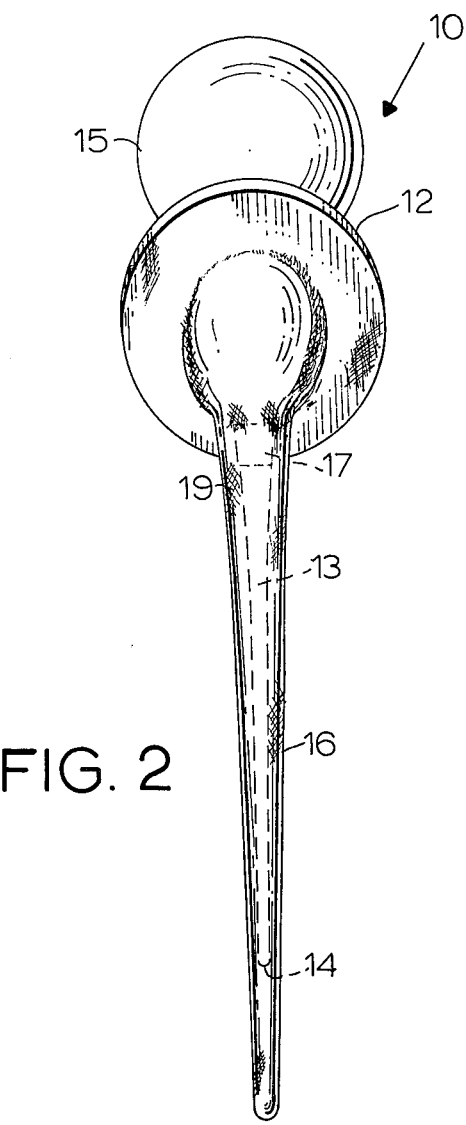
FIG. 2
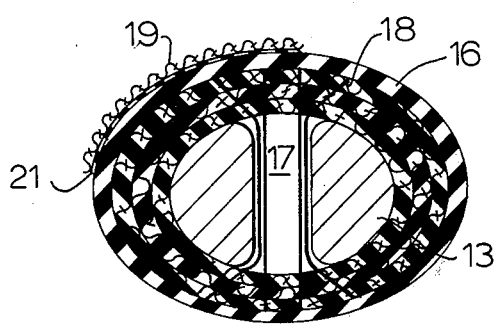
FIG. 3
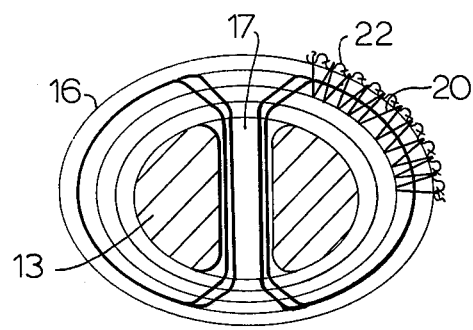
FIG. 3-A
INVENTOR.
PAUL KAHN
JAMES A. STUBSTAD
BY
Owen, Wickersham & Erickson
ATTORNEYS

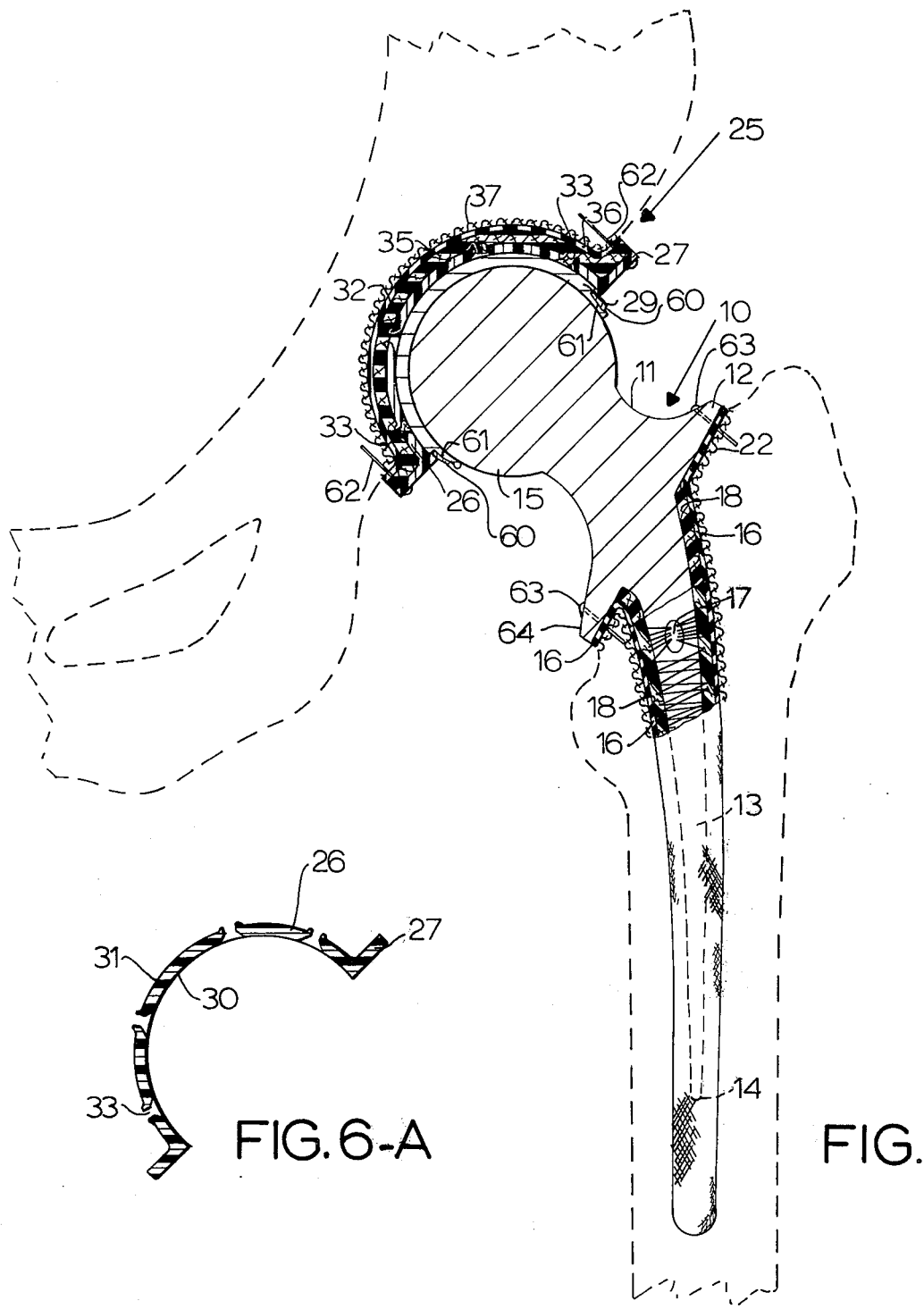
FIG. 6-A  FIG. 7

HIP JOINT PROSTHESIS

RELATED APPLICATION

This is a continuation of application Ser. No. 162,936, filed July 15, 1971, now abandoned, which was a continuation-in-part of application Ser. No. 60,804, filed Aug. 4, 1970, now abandoned.

BACKGROUND OF THE INVENTION

The repair of load-carrying skeletal members such as fractured bones, damaged or diseased joints, amputations, resections for malignancy or disease, and painful, malformed or otherwise mechanically affected skeletal components have hitherto been treated by the surgical techniques discussed below.

One most natural type of repair is autologous bone graft. Its use, however, exhibits at least one obvious, major deterrent, namely that of necessitating the complication of opening a second surgical site or bony sacrifice to provide the graft material. In addition, this type of repair requires special skill and improvisation on the part of the surgeon in fashioning the repair at the operating table within the time alloted for the surgery.

Various types of rigid and semi-rigid structurally splinted or stemmed devices have been used as bone replacement or as reinforcements or attachments to skeletal structure with varying degrees of success. Generally their use is initially very beneficial but over a period of years and months their efficacy often deteriorates because of loosening of the body attachment. It is believed that this effect results from high localized pressure loads imposed upon the bone by the hard-surfaced prosthetic material which tends to pinch off fine blood vessels and crush adjacent tissue, producing resorption of bone and necrotic degeneration in the affected zone. This effect is often noted only after the patient has been partially rehabilitated and attempts to put the affected limb or member into normal vigorous use.

At the forefront of current practice in this art are several techniques generally recognized as significant advancements in improving the biological compatibility of the prosthesis-to-bone interface and they are discussed below.

A. Bone cement.

This refers to an embedment system in which the metal stem of a prosthesis is cemented into intimate contact with porous hollow bone structure. A major advantage of this system is more uniform distribution of mechanical loads, elimination of relative motion between prosthesis and bone, and the achievement of much lower load per unit area (psi loading) than in devices of the earlier art, such lower loading more closely approaching the normal bone loading of undamaged natural skeletal structure. Problems associated with this technique include toxicity of the cement, necrosis of the adjacent bony layer due to heat of polymerization, incomplete filling of the cavity in the bone, and absence of resiliency.

B. Porous ceramic devices and porous ceramic coated metal stems.

This type of construction allows for a thin layer of tissue ingrowth into the pores and results in a very satisfactory type of biological interface where the brittle ceramics can be tolerated. Initial ingrowth of the patient's tissue into the prosthesis is, of necessity, fibrous and does not tend to develop calcium-rich bone until months or years postoperatively. Such ingrowth can be encouraged in the porous ceramic device by carefully controlled sandblasting to induce surface roughness while avoiding deep porosity with weakening of the ceramic structure. Since the tissue penetration is minimal, the joint strength is dependent on shear strength and resistance to cleavage in the thin fibrous attachment zone. Failure in either mode is usually complete and results in failure of the device. In addition, a shock mitigating resilient layer is absent.

C. Velour fiber coated metal stems.

The open literature reports over two years of animal testing involving partial limb replacement in amputations in which metal implants were velour-covered over a limited area at the distal end to obtain skin closure through tissue ingrowth. These tests did not make use of either full fabric jacketing or resilient cushioning. Therefore, the life of such implant does not usually exceed, and is often less than, six months. It is to be expected in such implants that even if it were fully fabric jacketed but without resiliency, in the longer term, the problems of rigid metal-to-bone interfacing would again be encountered after true bony fixation was obtained.

The above disadvantages are overcome and other advantages are also obtained by the present invention as will become apparent from the description below. This invention provides a strong, reinforced prosthesis which has a resilient, cushioning coating structure enclosing the reinforcement means, and a fibrous overlayer to encourage ingrowth of the patient's tissue and firm bonding of the prosthesis to the desired elements of the patient's or host structure. Thus, the device of this invention avoids the rigid or abrasive metal-to-bone facing, the brittleness of ceramic surfaces, has been observed to insert readily with minimal infection occurrences, and has exhibited good longevity in use in a patient. In addition, bonding of the components to each other is so efficiently and firmly effected in the present invention as to provide a reliable, load-bearing, high-strength transfer of loading from the reinforcing means across the elastomer jacket to the host bone.

SUMMARY OF THE INVENTION

The present invention concerns a prosthesis for the replacement of a damaged joint in an animal skeletal structure, particularly in a human skeletal structure; and more particularly it concerns a prosthesis comprising a shaped rigid core piece surrounded by an elastomeric, physiologically inert, cushioning body, and an outermost layer of a tissue ingrowth-receptive compatible open-pore fabric.

The shaped core reinforces the body to provide a load-bearing structure. When metal is employed as the core, it should be strong, lightweight, and resistant to attack by body fluids, such as titanium. Nonmetal cores may be rigid plastic.

A metal core may be shaped as by machining into the desired basic shape of the prosthesis to be made and then coated with the elastomer at least in the load-bearing areas to provide a resilient cushioned surface over the rigid core. In order to secure firm adhesion of the elastomer to the core, the surface of the core can be provided with gross holes or perforations for interlocking with the elastomer. Fibrous reinforcement for the elastomer, as will be later described, can be passed through holes in the rigid base to preferentially align with the stress axis of the primary load. Alternatively, the surface of the rigid core can be porous or chemically treated or etched, or it can be sandblasted, to promote adhesion of the elastomer or increase the effective surface of the core; or gross convolutions or irregularities can be provided on the rigid core surface to promote interlocking with the elastomer. Any desired combination of such treatment methods can be employed.

There are many devices in which the present invention can be used and the core can be shaped to conform to the desired use. Illustrative of these uses are the following devices made according to this invention, but without limiting the invention to such devices:

a. Stemmed hip joints.

b. Stemmed joints for knees, elbows, fingers, or toes.

c. Bone plates for use as replacements of articulating surfaces such as the knee (patella and tibial plateau) etc.

d. Bone plates and intramedullary nails or rods used for splinting fracures or performing joint arthrodesis.

e. Bone plates used for bone bridging as in major resections of the mandible in the case of trauma or cancer surgery.

f. Ceramic-coated metal-stemmed or metal-reinforced prostheses having a porous irregular ceramic surface for tissue ingrowth.

g. Devices utilizing ceramic, carbon, graphite and other rigid biologically inert prosthetic materials.

h. Devices using homograft and heterograft rigid bony transplant material prepared from human or animal donors.

i. Devices utilizing twisted metal strands or polymeric materials such as Dacron, nylon, Teflon (tetrafluoroethylene), polyethylene and the like hitherto used as thin bearing surfaces for joint lining as in the knee or hip, or as stiffening members in skeletal prostheses.

j. Implantable prosthetic teeth.

k. Calvarium replacement.

The core, base, or structural element may be metal, suitably titanium, but other inert materials such as disclosed above are also useful. In one form of the device the core is at least partially covered with, or embedded centrally in, a relatively thick coating body, or jacket of an elastomer, e.g. of silicone rubber (preferably medical grade), or other physiologically inert material. Preferably the elastomer is reinforced interiorly in addition to the core with inert fibrous material such as Dacron (polyethylene terephthalate), in a manner similar to that in which other load-bearing rubber or elastomer products, e.g. automobile tires, are reinforced to help them carry load, to restrict elongation, or to modify the stiffness of such products to match a given requirement. The fibers are suitably incorporated during the forming of the elastomer product or component by incorporating one or a plurality of layers of such fiber; or, less desirably, by random dispersal of such fibers through the elastomer mass. The layering procedure is preferred, and where the elastomer coating is applied to a metal or rigid material core having holes or apertures therein for affixation of the elastomer coating, some of the partially embedded fibers can, if desired, be passed through such holes to assist reinforcement. Preferably, the fibrous layer or fabric encapsulates and is attached to the metal reinforcing element where possible by suturing, by adhesive, or by prime coating or any combination thereof, and the whole is then co-molded with the elastomer, and with provision of a fabric-free layer of elastomer at the outer surface. An alternative technique can be used to incorporate the outer tissue-ingrowth fabric into the outer surface in a monolithic molding. The elastomeric body, layer, or coating is relatively thick, i.e. as thick as will be accommodated by the host site, to provide long-term cushioning of the bearing relationship between the host skeletal structure and the prosthesis, and, in some forms of the invention to share with the core the actual load bearing. Thickness of such coating in a femoral head prosthesis, for example, can be about 0.01 inch to 0.5 inch.

A layer of open-pore cloth fabric which is receptive to tissue ingrowth is disposed over the elastomer, i.e. at the surface thereof remote from the core, and is affixed thereto. Such a fabric can be velour, mesh, woven pile or the like, to invite tissue and bony ingrowth. One advantageous method of affixing the fabric to the elastomer is to coat the face of the fabric to be joined to such elastomer, e.g. by spraying, painting, dipping, or other desired method, with raw unvulcanized elastomer, especially silicone rubber, to partially impregnate the fabric. Sufficient depth of mesh or fiber surface is maintained free of the rubber to encourage the ingrowth mentioned above. About one-half of the depth of mesh or fiber surface is preferably maintained free of rubber. The impregnated fabric is then fitted over the prosthesis and smoothly affixed thereto by vulcanizing the elastomer impregnant, at a suitable temperature well known for the particular elastomer. When non-vulcanizing elastomers are employed, they are just heated beyond their melt temperature and then cooled. It will be understood that vulcanizing catalysts can be incorporated in the elastomer, if desired. Also, if desired, a water-or-solvent-soluble inert coating material, such as carboxymethylcellulose, methylcellulose, ethylcellulose, or mucilage can be first applied to the exterior face of the open-pore fabric by spraying or spreading of a thick solution of the barrier material to protect the pores of pile to the desired depth and keep them free of the rubber and is then dried, after which the fabric is subjected to the rubber-impregnation treatment. After impregnation molding and vulcanization are completed, the device is washed with water to remove remaining water-soluble coating from the exposed fibers.

Alternatively, an adhesive compatible with bony tissues as well as with the materials used in the construction of the prosthesis may be used to affix the tissue-ingrowth fabric. A further alternative, affixing the fabric and core to the elastomer by rubber impregnation as described above, the fabric, after application over the elastomer, can be sutured at its meshing edges or margins and at appropriate stress points, the sutures also extending into the elastomer. In special instances, the suture may pass through or around the internal stiffening members.

BRIEF DESCRIPTION OF DRAWINGS

The device or article of the present invention and some modes of carrying out the invention will also be illustrated by the annexed drawings, wherein:

FIG. 1 is a side elevational view of a femoral head prosthesis.

FIG. 2 is an elevational view of the device of FIG. 1 taken 90° to the right or, so-to-speak, a rear elevation.

FIG. 3 is a cross-sectional view of the stem of the device of FIG. 1, taken on line 3—3, exaggerated as to the reinforced elastomer coating.

FIG. 3a is another view like FIG. 3 but showing suturing of the fibrous layers and coating and only partially sectional, for clarity.

FIG. 6a is a similar cross-sectional view of the metal cup of FIG. 6 alone.

FIG. 7 is a sectional view of an artificial hip joint showing placement of the prostheses of FIGS. 1 to 6, when in use, the host skeletal structure being shown in phantom.

DETAILED DESCRIPTION OF THE INVENTION

Figure 4:
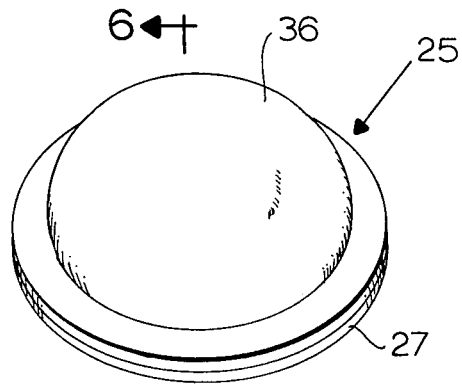
FIG. 4 is a top perspective view of an acetabulum prosthesis.

The invention will be described as to several embodiments illustrated in the accompanying drawings, like numerals being used to designate like parts.

In one embodiment of this invention, a femoral head prosthesis 10 as shown in FIGS. 1 through 3a comprises a femur head 15 having a neck 11 and base or shoulder 12, all formed of a suitable rigid plastic or metal, advantageously, in this embodiment, of titanium. Affixed to shoulder 12 or integral therewith is metal stem 13 which is of elongated conical shape, tapering to a small end 14 remote from shoulder 12 and being of sufficient length to extend a substantial distance into the medullary canal of a femur to be treated. Stem 13 is coated with a relatively thick layer 16 of silicone rubber, usually of about one-eighth inch in thickness, which completely coats all surfaces of stem 13 and extends beyond end 14 thereof, being also of elongated conical or tapering shape. Elastomer coating 16 is reinforced with a plurality of layers 18 of fiber, suitably Dacron fiber. Stem 13 is provided with an aperture 17 and in casting coating 16 onto stem 13 in some variants a portion of the fiber layers may be passed through aperture 17 to improve bonding and anchoring of coating 16 to stem 13. Advantageously, stem 13 is also fixed in place by sutures 20 which pass through at least several fibrous layers 18, around stem 13 and through aperture 17, as shown in FIG. 7 especially. Disposed on the surface of coating 16 is a layer 19 of open pore Dacron velour partially impregnated with and having an underlayer of elastomer 21 bonding the velour to the elastomer surface, the velour remaining open at its outer surface. However, FIG. 3a shows an alternative method of procedure wherein a layer of mesh fabric 22 is affixed to coating 16 by sutures 20 which pass through layer 22 and coating 16, passing also around one or more of reinforcing layers 18 so that sutures 20 are securely anchored and in turn firmly hold and affix mesh layer 22.

Figure 5:
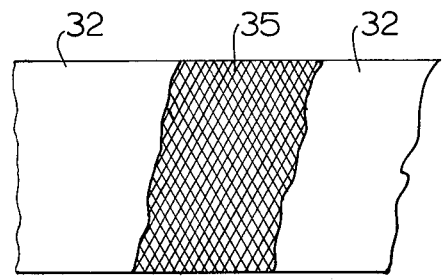
FIG. 5 is a top view, cut away in layers and showing in detail the structure of the reinforced elastomer, of the device of FIG. 4.
Figure 6:
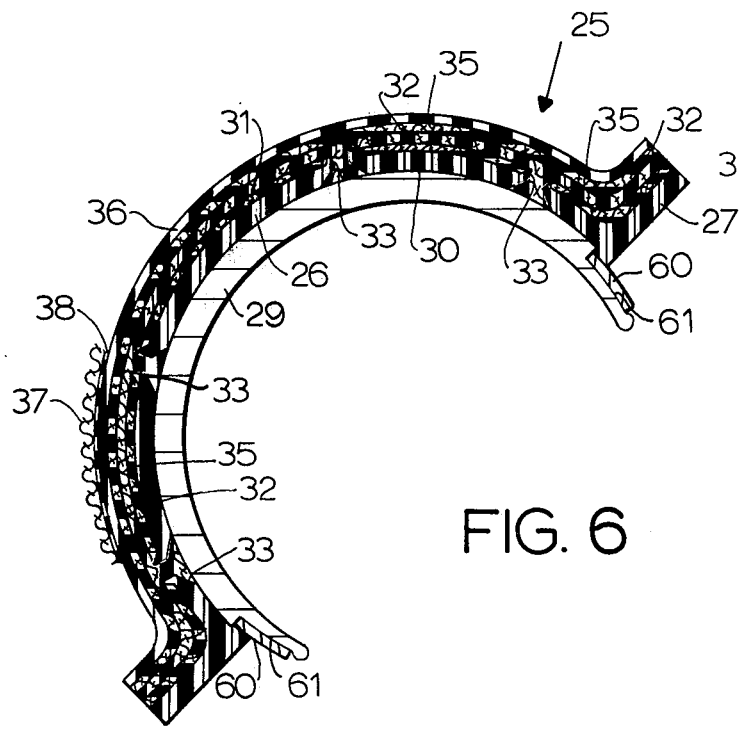
FIG. 6 is a cross-sectional view of the device of FIG. 4, taken on line 6—6.

FIGS. 4 through 6 illustrate an acetabulum prosthesis 25, which comprises a titanium metal reinforcing cup 26 of hemispherical shape and having an angular flange 27 at its base. A bearing surface 29 of suitable hard, physiologically inert polymeric material, advantageously of Teflon (tetrafluoroethylene), polyethylene, polypropylene, or the like is affixed to inner or concave face 30 of cup 26 by means of medical rubber cement, or retained by other suitable means. Disposed on convex face 31 of cup 26 is relatively thick elastomer coating or cushion 32 contoured to face 31 and extending over and supported by flange 27. A plurality of apertures 33 are provided in cup 26 in this embodiment to key coating 32 to cup 26 and assist in affixing it firmly thereto. A plurality of layers 35 of Dacron fibers are disposed within coating 32 as reinforcing elements. In order to affix coating 32 to face 31 it will be understood that alternatively or in addition to apertures 33, face 31 can be chemically primed; or can be sandblasted to provide greater surface area, or both. Disposed at the exterior face 36 of coating 32 is velour layer 37, affixed to coating 32 by an elastomer underlayer 38 as in FIGS. 1–3.

FIG. 7 shows the placement and coaction of femoral head prosthesis 10 and acetabulum prosthesis 25, the stem of prosthesis 10 being inserted in the medullary canal of a femur and shoulder 12 being supported on the shoulder thereof, while prosthesis 25 is placed in a corresponding cup-shaped depression in the outer surface of a hipbone (bones being shown in phantom). A metal band 60 is secured around the member 29 in a recess 61. Temporary means for retention of the prostheses in the cavities during the period of initial ingrowth may be used as necessary. Pins 62 through the flange 27 and pins 63 through the flange 64 may serve this function.

In making the prosthesis of this invention, the device is suitably molded to the desired shape, depending upon the joint to which it is to be applied such as elbow, hip, knee, finger, toe, or other, especially the load-bearing sites or those likely to be under high stress in an animal or human body. The reinforcing fabric layer or multiple layers are in place in the mold, along with the plastic or metal reinforcing member pre-treated as indicated above if desired, and the mold is filled with the elastomer, advantageously a silicone rubber, and solidified to form the desired shaped base prosthesis. Other physiologically compatible elastomers can be used instead of the silicone rubber. The size of each prosthesis is tailored to the body into which it is to be inserted.

The tissue ingrowth-receptive, open pore fabric is suitably thereafter applied to the formed base prosthesis. As mentioned above, this is advantageously done by partially impregnating the fabric, i.e. at its inner surface and partially through the open pores or fibers, sufficient openings remaining to effect firm bonding by ingrowth of tissue or bony structure. Such impregnation may be done by any of several alternative techniques:

1. Pressure impregnation.

Raw unvulcanized rubber is hydraulically pressed into pile fabric between matched mold faces. This is optimally done at room temperature in fabrics of ½ to 1 millimeter thickness at contact pressures from 100 to 500 psi for periods of 5 to 15 minutes under pressure. Minimum delay is exercised in accomplishing forming and vulcanizing in order to minimize migration of silicone by wicking action into the tissue interface zone of the cloth.

2. Dispersion coating.

Improved wetting of cloth fibers and improved bond strength approximating the full strength of silicone rubber is obtained by dissolving raw silicone rubber with a suitable fugitive solvent (chloroform) so that it may be spread into intimate contact with the pile fabric, filling fine interstices to create an improved bonding surface.

3. Medical adhesives.

Commercially prepared silicone rubber adhesives which are specially compounded to cure in closed wounds or open air by hydrolizing with available moisture may be spread on pile fabric to achieve a bond between cloth and prosthesis. Generally, however, these adhesives are of low strength due to their particular chemistry and can be used only in limited circumstances.

4. Suturing.

Surface interfacing cloth may be directly attached to the prosthesis with sutures (Dacron) without use of any rubbery bonding material. Sutures are placed along joining margins and in appropriate stress points. Sutures need not be tight, allowing for a finite amount of freedom to invite deeper invasion by ingrowth tissue. Sutures may be arranged in "X" pattern to encircle metal reinforcement or to provide limited flexibility by flexure of the "X" pattern similar to accordion motion.

5. Preferred attachment techniques are combinations of items 1, 2, and 4, but with a safety factor added in the form of a soluble inert coating which may first be applied to the physiological interface of the cloth to inhibit undesirable impregnation of the fibers with silicones which inhibit tissue attachment. (A typical inert coating is carboxy ethyl cellulose.) This coating material may be used in either of two ways;

1. Optimally, it is coated on the fabric and laid directly into the female cavities of the prosthesis mold enabling a monolithic one-step operation.

2. The coating may be first applied to fabric, dried, then hydraulically impregnated or dispersion coated with silicone rubber, then applied to a pre-formed prosthesis.

Surgical insertion of the prosthesis is accomplished with conventional techniques.

The above specific description and drawings have been given for purposes of illustration only and modifications and variations can be made therein without departing from the spirit and scope of the appended claims. Where "rubber," "rubbery elastomer" or "elastomer" are mentioned herein, it will be understood that medical grade material is meant; and an especially useful material is available in commerce after the trademark "Silastic" (Dow Corning Co.).

Having now described the invention, what is claimed is:

1. A hip prosthesis for repairing a damaged hip joint in an animal skeletal structure, comprising in combination:
   I. an acetabulum prosthesis having
      a. a hemispherical metal cup having an exterior annular flange at its base, a concave surface and a convex surface,
      b. a relatively thick cushioning layer of an elastomer disposed over and covering said convex face and said flange,
      c. an open pore, physiologically inert coating of fabric disposed over and covering said elastomer, and adapted to receive host tissue ingrowth,
      d. said cup, said elastomer and said coating all being firmly bonded to each other, and
   II. a femoral head prosthesis having a ball at one end, said ball fitting in said cup.

2. The prosthesis of claim 1 wherein the concave surface of the metal cup has affixed to it a polymeric surface adapted to receive and coact with said femoral head.

3. The prosthesis of claim 2 wherein said polymeric surface's annular flange lies beyond the arc of the hemisphere and has an annular exterior recess, and a metal band in said recess retaining said ball in said cup.

4. The prosthesis of claim 3 wherein said metal cup has a radial flange extending around said cup, for securing pins for temporary anchoring to bone structure.

5. A hip prosthesis for repairing a damaged hip joint in an animal skeletal structure, comprising in combination:
   I. an acetabulum prosthesis having
      a. a hemispherical metal cup having an exterior annular flange at its base, a concave surface and a convex surface,
      b. a relatively thick cushioning layer of an elastomer disposed over and covering said convex face and said flange,
      c. an open pore, physiologically inert coating of fabric disposed over and covering said elastomer, and adapted to receive host tissue ingrowth, and
      d. said cup, said elastomer and said coating all being firmly bonded to each other, and
   II. a femoral head prosthesis having a ball at one end, said ball fitting in said cup, said femoral head prosthesis comprising
      a. a stem adapted to be inserted into a medullary canal of a bone of said structure,
      b. a reinforcing core extending into said stem,
      c. a cushioning coating of elastomer over said core, secured to and at least partially enclosing the same, and
      d. a surface covering of open-pore material secured to said elastomer and adapted to receive host tissue ingrowth.

6. A femoral head prosthesis, including in combination:
   a. a rigid ball member,
   b. a rigid stem core member extending from said ball member and integral therewith,
   c. a cushioning coating of elastomer secured to and at least partially enclosing said stem core member, and
   d. a surface layer of fibrous material capable of receiving tissue ingrowth secured to at least a portion of said elastomer.

* * * * *